(12) United States Patent
Multer

(10) Patent No.: US 11,730,990 B2
(45) Date of Patent: *Aug. 22, 2023

(54) FLEXIBLE DRY SPRINKLER HAVING A DIFFERENTIAL PRESSURE CONTROLLER

(71) Applicant: The Reliable Automatic Sprinkler Co. Inc., Liberty, SC (US)

(72) Inventor: Thomas Multer, Liberty, SC (US)

(73) Assignee: The Reliable Automatic Sprinkler Co. Inc., Liberty, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/341,662

(22) Filed: Jun. 8, 2021

(65) Prior Publication Data

US 2021/0290999 A1 Sep. 23, 2021

Related U.S. Application Data

(63) Continuation of application No. 15/989,316, filed on May 25, 2018, now Pat. No. 11,083,920, which is a
(Continued)

(51) Int. Cl.
*A62C 37/11* (2006.01)
*A62C 35/68* (2006.01)
(Continued)

(52) U.S. Cl.
CPC ............. *A62C 37/11* (2013.01); *A62C 3/004* (2013.01); *A62C 35/68* (2013.01); *A62C 35/60* (2013.01); *A62C 35/62* (2013.01); *A62C 37/14* (2013.01)

(58) Field of Classification Search
CPC ......... A62C 37/10; A62C 37/11; A62C 37/14; A62C 35/64; A62C 35/68; A62C 35/60; A62C 35/62
See application file for complete search history.

(56) References Cited

U.S. PATENT DOCUMENTS

| 1,405,411 A | 2/1922 | Hamilton |
| 3,329,215 A | 7/1967 | Kane |

(Continued)

FOREIGN PATENT DOCUMENTS

| WO | 2012/166636 A1 | 12/2012 |
| WO | 2012/166644 A1 | 12/2012 |

OTHER PUBLICATIONS

Viking, Easy Riser Swing Check Valve, Models E-1 & F-1, http://www.vikingcorp.com/sites/default/files/documents/011189_0.pdf.
(Continued)

*Primary Examiner* — Christopher R Dandridge
(74) *Attorney, Agent, or Firm* — Venable LLP

(57) ABSTRACT

A dry sprinkler includes a flexible tube section that maintains a pressurized fluid, such as a liquid antifreeze solution, between a first end and a second end. A first seal prevents fluid from a supply line from entering the flexible tube section. The first seal is maintained in a sealed position by a pressure of the pressurized fluid. A sprinkler head is coupled to the second end of the flexible tube section, and includes a frame, an output orifice, a deflector, a second seal that seals the output orifice, and a thermally responsive element configured to maintain the second seal in a sealed position when the thermally responsive element is in a non-responsive state. A differential pressure controller maintains a ratio between the pressure of the pressurized fluid in the flexible tube section and a pressure of a supply fluid in the supply line to at least a certain ratio.

45 Claims, 1 Drawing Sheet

Related U.S. Application Data continuation of application No. 13/757,148, filed on Feb. 1, 2013, now Pat. No. 8,921,324.

(60) Provisional application No. 61/594,972, filed on Feb. 3, 2012.

(51) Int. Cl.
*A62C 37/14* (2006.01)
*A62C 35/62* (2006.01)
*A62C 3/00* (2006.01)
*A62C 35/60* (2006.01)

(56) References Cited

U.S. PATENT DOCUMENTS

| | | |
|---|---|---|
| 6,488,097 B1 | 12/2002 | MacDonald, III et al. |
| 7,389,824 B2 | 6/2008 | Jackson |
| 7,802,628 B1 | 9/2010 | Silva, Jr. et al. |
| 11,083,920 B2 * | 8/2021 | Multer .................. A62C 37/11 |
| 2003/0075343 A1 * | 4/2003 | Ballard .................. A62C 3/004 |
| | | 169/37 |
| 2009/0254315 A1 | 10/2009 | Golinveaux |
| 2010/0038099 A1 | 2/2010 | Thompson et al. |
| 2011/0127049 A1 | 6/2011 | Long |
| 2012/0031630 A1 | 2/2012 | Stephens |
| 2012/0298383 A1 | 11/2012 | Shipman |

OTHER PUBLICATIONS

Office Action dated Feb. 27, 2019, issued in corresponding Korean Patent Application No. 10-2013-0011858.

* cited by examiner

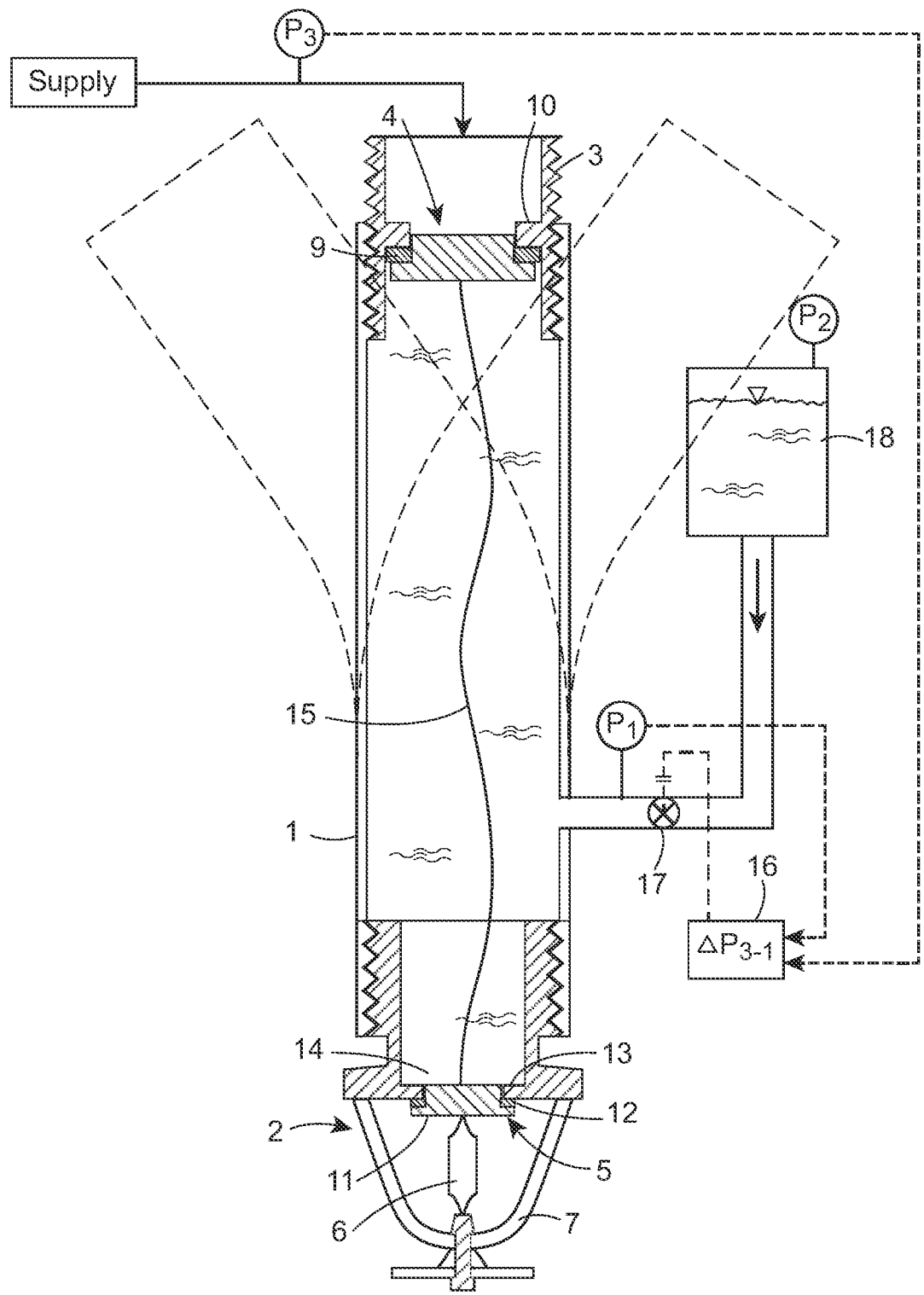

FLEXIBLE DRY SPRINKLER HAVING A DIFFERENTIAL PRESSURE CONTROLLER

CROSS REFERENCE TO RELATED APPLICATIONS

This application is a continuation of U.S. patent application Ser. No. 15/989,316, filed May 25, 2018, now U.S. Pat. No. 11,083,920, issued on Aug. 10, 2021, which is a continuation of U.S. patent application Ser. No. 13/757,448, filed Feb. 1, 2013, now U.S. Pat. No. 9,999,793, issued on Jun. 19, 2018, and which claims priority to U.S. Provisional Patent Application No. 61/594,972, filed Feb. 3, 2012, each of which is incorporated herein by reference in its entirety.

FIELD OF THE INVENTION

My invention relates to a dry fire protection sprinkler. In particular, my invention relates to a dry fire protection sprinkler for use in an area that is exposed to freezing conditions. In addition, my invention relates to a dry fire protection sprinkler having a differential pressure controller.

BACKGROUND OF THE INVENTION

Dry sprinklers are used in areas that are exposed to freezing conditions, such as in freezers or outdoor walkways. In some dry-pipe systems, fluid supply conduits are positioned in a space in which the fluid in the fluid supply conduit is not subject to freezing. A dry sprinkler is attached to the fluid supply conduit and extends into a space in which the fluid would otherwise be subject to freezing.

A typical dry sprinkler comprises a sprinkler head, a tube, a pipe connector at an inlet end of the tube that connects the inlet end to a pipe network of a fire suppression system, a plug seal at the inlet end to prevent water from entering the tube, and an actuating mechanism to maintain the plug seal at the inlet end. Typically, the sprinkler head is attached to an end of the tube that is opposite to the inlet end of the tube. Also, the tube section is conventionally vented to the atmosphere to allow drainage of any condensate that may form in the tube.

Examples of dry sprinklers are generally disclosed in U.S. Pat. No. 5,775,431 to Ondracek, and in U.S. Pat. No. 5,967,240 to Ondracek. As shown generally in these patents, the actuating mechanism of a dry sprinkler can be a rod or another similar structure that extends through the tube between the sprinkler head and the inlet end to maintain the plug seal at the inlet end. The actuating mechanism includes a thermally responsive support element at the sprinkler head that supports the rod and, therefore, the plug seal at the inlet end. In some dry sprinklers, the tube is also sealed at the sprinkler head end of the tube and the actuating mechanism is supported at the sprinkler head end by a seal cap that is supported by the thermally responsive support element. In such arrangements, the space in the tube between the seal cap and the plug seal can be filled with a pressurized gas, such as dry air or nitrogen, or with a liquid, such as an antifreeze solution. When an elevated temperature occurs, the thermally responsive support element fails, releasing the plug seal (and also any lower seal at the sprinkler head end of the tube) to allow water from the fluid supply conduit to flow into and through the tube to the sprinkler head, whereupon the fluid is distributed by the sprinkler head.

Conventional dry sprinklers are fabricated using a rigid tube having a seal at the inlet that is separated from the thermally responsive support element of the sprinkler, which is intended to be positioned in an area exposed to freezing conditions, such as an area that is not heated. The rigid tube extends into the unheated area from a wet pipe system (located in a heated area) and must be precisely aligned and installed while avoiding various architectural, structural, and mechanical obstructions typically found in commercial or industrial buildings.

SUMMARY OF THE INVENTION

To remedy the problems and difficulties noted above, in one aspect, the invention provides a dry sprinkler having a flexible tube section that has a first end having an inlet opening, and a second end having an outlet opening. The flexible tube section is configured to contain a pressurized fluid between the first end and the second end. The pressurized fluid includes a liquid anti-freeze solution that is not susceptible to freezing at the freezing point of water. The dry sprinkler includes a supply line connection having a first end connected to the inlet opening of the first end of the flexible tube section and having an opening, and a second end configured to connect to a supply line to receive a supply fluid from the supply line. A first seal is configured to seal the opening at the first end of the supply line connection to prevent the supply fluid from the supply line from entering the flexible tube section. The first seal is maintained in a sealed position by a pressure of the pressurized fluid so as to seal the opening at the first end of the supply line connection. A sprinkler head is coupled to the second end of the flexible tube section. The sprinkler head has a frame connected to the second end of the flexible tube section, an output orifice centrally located within the frame, a deflector connected to the frame, a second seal configured to seal the output orifice of the sprinkler head, and a thermally responsive element between the frame and the second seal. The thermally responsive element is configured to maintain the second seal in a sealed position when the thermally responsive element is in a non-responsive state. A differential pressure controller is connected to the flexible tube section between the first seal and the second seal, and is connected to the supply line connection. The differential pressure controller is configured to supply the pressurized fluid to the flexible tube section in order to maintain a ratio between the pressure of the pressurized fluid in the flexible tube section and a pressure of the supply fluid in the supply line to at least a certain ratio. The pressure of the pressurized fluid in the flexible tube section is not equal to the pressure of the supply fluid in the supply line. The thermally responsive element is configured to switch from the non-responsive state to a responsive state to release the second seal in response to an elevated temperature condition, and to permit the release of the pressurized fluid in the flexible tube section. The release of the pressurized fluid in the flexible tube section releases the first seal from the seal position.

BRIEF DESCRIPTION OF THE DRAWING

FIG. 1 shows a flexible dry sprinkler in accordance with an embodiment of the invention.

DETAILED DESCRIPTION OF THE PREFERRED EMBODIMENTS

As shown in FIG. 1, a flexible dry sprinkler arrangement comprises a generally flexible tube 1 that is connected at one end to a sprinkler head 2 and connected at another end to a fitting 3 constructed to be coupled to a wet pipe, a dry pipe, or a preaction fire sprinkler system. The fitting 3 includes an inlet seal assembly having a first seal 4 that is normally in a closed or sealed position for preventing the flow of fluid from the fitting 3 through the flexible tube 1 and the sprinkler head 2. The flexible tube 1 is also sealed at the sprinkler head 2 by an outlet seal assembly having a second seal 5 (e.g., a sealing cap) that is supported by a thermal release element 6 compressed between the second seal 5 and a frame 7 of the sprinkler head 2. The first seal 4 is generally formed as an annular plug having a grooved outer edge that sits against an annular spring washer 9 of the inlet seal assembly, such as a Belleville washer. The annular spring washer 9 is configured to seal with an annular flange 10 extending from an inner wall of the fitting 3. The second seal 5 is formed similarly to the first seal 4, and also is generally formed as an annular disk 11 having an outer annular groove that receives a spring washer 12 of the outlet seal assembly. The spring washer 12 is constructed to seal against a sealing flange 13 formed in an output orifice 14 of the sprinkler head 2.

The flexible tube 1 can be formed from a metallic or a non-metallic material. For example, in one embodiment, the flexible tube 1 is formed from a corrugated metal hose, and, in another embodiment, the flexible tube 1 is formed from a corrugated plastic hose. The outer surface of the flexible tube 1 can be covered, such as with a braided jacket, to protect the flexible tube 1. As shown in the preferred embodiment, the sprinkler head 2 has male threads that engage with female threads on the output end of the flexible tube 1. The female threaded connection of the flexible tube 1 can have a nominal diameter that is between ½ inch and 1 inch. While a specific configuration of the sprinkler head 2 is shown in FIG. 1, the present disclosure is broader than this configuration, and it is contemplated that substantially any present or future approved or listed fire sprinkler head can be attached to the flexible tube 1 in place of the sprinkler head 2 shown in FIG. 1.

When the flexible dry sprinkler is in a sealed state, as shown in FIG. 1, the flexible dry sprinkler is filled with a fluid that is pressurized to keep the first seal 4 sealed. The fluid is a freeze resistant gas, such as nitrogen, or a liquid, such as a water/glycol mixture or other conventional "antifreeze" liquids.

The connection to the fire sprinkler system utilizes a differential pressure device 16 to ensure the pressure in the flexible tube 1 is greater than the pressure in the fluid supply so as to prevent the introduction of water or air from the fire sprinkler system into the flexible tube 1. This differential pressure device 16 is configured to maintain a ratio of 3 to 1 or greater between the pressure P1 in the flexible tube 1 and the fluid supply pressure P3 in the fluid supply. It is believed that the ratio of 3 to 1 is sufficient to prevent leakage into the flexible tube 1 caused by pressure surges in the fluid supply of the fire sprinkler system. In one embodiment, the differential pressure device 16 is configured as a differential pressure controller in communication with a pressure sensor that monitors the fluid supply pressure P3 and in communication with a pressure sensor that monitors the pressure P1. The differential pressure controller 16 is in communication with a control valve 17 positioned between the flexible tube 1 and a source of pressurized fluid 18 that is maintained at a pressure P2 that is greater than the fluid supply pressure P3. In the event that the pressure ratio drops below 3 to 1, a signal is sent from the differential pressure controller 16 to the control valve 17 to open the control valve 17 to introduce the pressurized fluid from the source of pressurized fluid 18 into the flexible tube 1 until the 3 to 1 ratio is achieved, at which time the control valve 17 is instructed to close. Thus, the differential pressure controller 16 and the control valve 17 operate according to a conventional feedback control arrangement to maintain the desired pressure ratio, e.g., of 3 to 1. It will be appreciated that the differential pressure controller 16 may include a computer constructed to execute a computer readable program stored in a tangible computer-readable medium or in another type of memory, and including instructions for operating the differential pressure controller 16 to maintain the pressure ratio between P1 and P3. While one embodiment of a control arrangement has been described with reference to the preferred embodiment, other control arrangements can be employed to maintain the desired pressure ratio, and are within the scope of this disclosure.

Moreover, the various pressure sensors that monitor the pressures P1, P2, and P3 can be constructed to communicate with an alarm system to notify an operator regarding operation of the fire sprinkler system. For example, an alarm may be provided to notify an operator if the pressure P1 decreases to a certain pressure value, which may alert the operator of the possibility that the sprinkler head 2 may be leaking. Alternatively, notifications can be provided by various methods, including, but not limited to, a telephone message, an e-mail, a visual display, and a facsimile message. Optionally, a visual pressure indicator, such as an analog or digital pressure gauge, located proximate to the flexible dry sprinkler, can be installed for indication that the pressure P1 of the fluid sealed in the flexible tube 1 has been maintained within tolerances permitted by the design of the flexible dry sprinkler. Such an indicator may simply be a binary status indicator, such as a color indicator, e.g., an indicator that displays green, indicating acceptable operating status, and that displays red, indicating an unacceptable operating status. Of course, other pressure indicators are within the scope of this disclosure.

An optional flexible linkage 15 is shown in FIG. 1 connecting the first seal 4 to the second seal 5. The flexible linkage 15 is formed of a material that will not corrode in the presence of the fluid contained in the flexible tube 1. The flexible linkage 15 can be formed as a chain or a cable. In one exemplary embodiment, the flexible linkage 15 is constructed of stainless steel. By virtue of the flexible linkage 15, when the flexible tube 1 of the flexible dry sprinkler is bent, as shown by the broken lines, the flexible linkage 15 in the flexible tube 1 will conform to the inner wall of the flexible tube 1 and will not limit the range of motion of the flexible tube 1. Also, by physically coupling the first seal 4 and the second seal 5 together with the flexible linkage 15, the first seal 4 can be pulled out of the flexible tube 1 by virtue of the release and discharge of the second seal 5. It is expected that the flexible linkage 15 will positively ensure that the first seal 4 is indeed removed from the path of flow in the flexible tube 1 without being obstructed by other structures in the flexible tube 1. Also, the flexible linkage 15 allows the first seal 4 to pass out of the flexible tube 1 regardless of any kinks or sharp corners in the inner surface of the flexible tube 1 caused by corrugations in the flexible tube 1 or flexing of the flexible tube 1.

The flexibility in the flexible tube 1 of the flexible dry sprinkler facilitates installation of the sprinkler system because the flexible dry sprinkler can be moved around building obstructions that would ordinarily require additional plumbing work. Moreover, the flexibility of the flexible dry sprinkler eliminates the need for installers of the fluid supply to precisely align the sprinkler drops (i.e., the connections for each flexible dry sprinkler) in the ceiling of a structure because any variance can be adjusted by movement of the flexible tube 1.

While the present invention has been described with respect to what are, at present, considered to be the preferred embodiments, it is to be understood that the invention is not limited to the disclosed embodiments. To the contrary, the invention is intended to cover various modifications and equivalent arrangements included within the spirit and scope of the appended claims.

INDUSTRIAL APPLICABILITY

My invention can be used to provide fire protection, particularly in areas subject to freezing conditions. Thus, the invention is applicable to the fire protection industry.

I claim:

1. A dry fire protection sprinkler comprising:
   a flexible tube having an inlet end, an outlet end, and a valve opening, and configured to contain a pressurized fluid;
   a sprinkler frame connected to the outlet end of the flexible tube, and having an outlet orifice;
   an outlet seal assembly having a sealing cap and a spring washer that are configured to seal the outlet orifice of the sprinkler frame, wherein the flexible tube contains the pressurized fluid between an inlet seal assembly and the sealing cap of the outlet seal assembly;
   a thermally responsive element provided between the sprinkler frame and the sealing cap of the outlet seal assembly, the thermally responsive element being configured to fail when ambient temperature reaches a predetermined temperature, and to hold the sealing cap of the outlet seal assembly in an outlet orifice until the thermally responsive element fails;
   a flexible tube pressure sensor configured to measure a pressure P1 of the pressurized fluid in the flexible tube;
   a control valve connected to the valve opening of the flexible tube, and configured to open and to close;
   a pressurized fluid source connected to the control valve and configured to supply the pressurized fluid to the flexible tube when the control valve opens, the pressurized fluid in the pressurized fluid source being at a pressure P2;
   a fluid supply pressure sensor configured to measure a pressure P3 of the pressurized fluid in the fluid supply line, the pressure P2 of the pressurized fluid in the pressurized fluid source being greater than the pressure P3 of the fluid in the supply line; and
   a differential pressure controller connected to the control valve, to the flexible tube pressure sensor, and to the fluid supply pressure sensor, and, when a ratio of the pressure P1 of the pressurized fluid in the flexible tube to the pressure P3 of the fluid in the fluid supply line is less than a predetermined ratio of at least 3 to 1, the differential pressure controller sends a signal to the control valve to open, in order to allow the pressurized fluid in the pressurized fluid source at the pressure of P2 to enter the flexible tube, and, when the ratio of the pressure P1 of the pressurized fluid in the flexible tube to the pressure P3 of the fluid in the fluid supply line equals the predetermined ratio, the differential pressure controller sends a signal to the control valve to close.

2. The dry fire protection sprinkler according to claim 1, wherein the sprinkler frame has frame arms that form a hub that is spaced from the outlet orifice.

3. The dry fire protection sprinkler according to claim 2, further comprising a deflector connected to the hub of the sprinkler frame.

4. The dry fire protection sprinkler according to claim 1, wherein the outlet end of the flexible tube is threadably connected to the sprinkler frame.

5. The dry fire protection sprinkler according to claim 1, further comprising a pressure indicator connected to the flexible tube, the pressure indicator being configured to indicate the pressure of the pressurized fluid in the flexible tube.

6. The dry fire protection sprinkler according to claim 5, wherein the pressure indicator is at least one of an analog pressure monitor and a digital pressure monitor.

7. The dry sprinkler according to claim 5, wherein the pressure indicator is constructed to communicate with an alarm system.

8. The dry fire protection sprinkler according to claim 7, wherein the alarm system notifies an operator if the pressure of the pressurized fluid in the flexible tube decreases to a certain pressure value.

9. The dry fire protection sprinkler according to claim 1, further comprising a flexible connector provided in the flexible tube and connected to the sealing cap of the outlet seal assembly.

10. The dry fire protection sprinkler according to claim 9, wherein the flexible connector is one of a chain and a cable.

11. The dry fire protection sprinkler according to claim 1, wherein the flexible tube is a corrugated metal hose.

12. The dry fire protection sprinkler according to claim 1, wherein the flexible tube is a corrugated plastic hose.

13. The dry fire protection sprinkler according to claim 1, wherein the spring washer of the outlet seal assembly is provided in the outlet orifice of the sprinkler frame, and the sealing cap of the outlet seal assembly is an annular disk that sits in the spring washer of the outlet seal assembly.

14. The dry fire protection sprinkler according to claim 13, wherein the annular disk of the outlet seal assembly has an annular groove, and the spring washer of the outlet seal assembly is positioned in the annular groove.

15. A dry fire protection sprinkler comprising:
   an inlet seal assembly;
   a flexible tube having an inlet end, an outlet end, and a valve opening, and configured to contain a pressurized fluid, wherein the flexible tube has a circular inner cross section; a sprinkler frame connected to the outlet end of the flexible tube, and having an outlet orifice; an outlet seal assembly having a sealing cap and a spring washer that are configured to seal the outlet orifice of the sprinkler frame, wherein the flexible tube contains the pressurized fluid between the inlet plug of the inlet seal assembly and the sealing cap of the outlet seal assembly; a thermally responsive element provided between the sprinkler frame and the sealing cap of the outlet seal assembly, the thermally responsive element being configured to fail when ambient temperature reaches a predetermined temperature, and to hold the sealing cap of the outlet seal assembly in the outlet orifice until the thermally responsive element fails; a flexible tube pressure sensor configured to measure a pressure P1 of the pressurized fluid in the flexible tube; a control valve connected to the valve opening of the flexible tube, and configured to open and to close; a pressurized fluid source connected to the control valve and configured to supply the pressurized fluid to the flexible tube when the control valve opens, the pressurized fluid in the pressurized fluid source being at a pressure P2; a fluid supply pressure sensor configured to measure a pressure P3 of the pressurized fluid in the fluid supply line, the pressure P2 of the pressurized fluid in the pressurized fluid source being greater than the pressure P3 of the fluid in the supply line; and a differential pressure controller connected to the control valve, to the flexible tube pressure sensor, and to the fluid supply pressure sensor, and, when a ratio of the pressure P1 of the pressurized fluid in the flexible tube to the pressure P3 of the fluid in the fluid supply line is less than a predetermined ratio of at least 3 to 1, the differential pressure controller sends a signal to the control valve to open, in order to allow the pressurized fluid in the pressurized fluid source at the pressure of P2 to enter the flexible tube, and, when the ratio of the pressure P1 of the pressurized fluid in the flexible tube to the pressure P3 of the fluid in the fluid supply line equals the predetermined ratio, the differential pressure controller sends a signal to the control valve to close.

16. The dry fire protection sprinkler according to claim 15, wherein the sprinkler frame has frame arms that form a hub that is spaced from the outlet orifice.

17. The dry fire protection sprinkler according to claim 16, further comprising a deflector connected to the hub of the sprinkler frame.

18. The dry fire protection sprinkler according to claim 15, wherein the outlet end of the flexible tube is threadably connected to the sprinkler frame.

19. The dry fire protection sprinkler according to claim 15, further comprising a pressure indicator connected to the flexible tube, the pressure indicator being configured to indicate the pressure of the pressurized fluid in the flexible tube.

20. The dry fire protection sprinkler according to claim 19, wherein the pressure indicator is at least one of an analog pressure monitor and a digital pressure monitor.

21. The dry sprinkler according to claim 19, wherein the pressure indicator is constructed to communicate with an alarm system.

22. The dry fire protection sprinkler according to claim 21, wherein the alarm system notifies an operator if the pressure of the pressurized fluid in the flexible tube decreases to a certain pressure value.

23. The dry fire protection sprinkler according to claim 15, further comprising a flexible connector provided in the flexible tube and connected to the inlet plug of the inlet seal assembly and the sealing cap of the outlet seal assembly.

24. The dry fire protection sprinkler according to claim 23, wherein the flexible connector is one of a chain and a cable.

25. The dry fire protection sprinkler according to claim 15, wherein the flexible tube is a corrugated metal hose.

26. The dry fire protection sprinkler according to claim 15, wherein the flexible tube is a corrugated plastic hose.

27. The dry fire protection sprinkler according to claim 15, wherein the spring washer of the outlet seal assembly is provided in the outlet orifice of the sprinkler frame, and the sealing cap of the outlet seal assembly is an annular disk that sits in the spring washer of the outlet seal assembly.

28. The dry fire protection sprinkler according to claim 27, wherein the annular disk of the outlet seal assembly has an annular groove, and the spring washer of the outlet seal assembly is positioned in the annular groove.

29. A dry fire protection sprinkler for use in an area that is exposed to freezing conditions, the dry fire protection sprinkler comprising:

a flexible tube having an inlet end, an outlet end, and a valve opening, and configured to contain a pressurized fluid, the pressurized fluid being a liquid anti-freeze solution that is not susceptible to freezing at the freezing point of water;

a sprinkler frame connected to the outlet end of the flexible tube, and having an outlet orifice;

an outlet seal assembly having a sealing cap and a spring washer that are configured to seal the outlet orifice of the sprinkler frame, wherein the flexible tube contains the pressurized fluid between an inlet seal assembly and the sealing cap of the outlet seal assembly;

a thermally responsive element provided between the sprinkler frame and the sealing cap of the outlet seal assembly, the thermally responsive element being configured to fail when ambient temperature reaches a predetermined temperature, and to hold the sealing cap of the outlet seal assembly in the outlet orifice until the thermally responsive element fails;

a flexible tube pressure sensor configured to measure a pressure P1 of the pressurized fluid in the flexible tube;

a control valve connected to the valve opening of the flexible tube, and configured to open and to close;

a pressurized fluid source connected to the control valve and configured to supply the pressurized fluid to the flexible tube when the control valve opens, the pressurized fluid in the pressurized fluid source being at a pressure P2;

a fluid supply pressure sensor configured to measure a pressure P3 of the pressurized fluid in the fluid supply line, the pressure P2 of the pressurized fluid in the pressurized fluid source being greater than the pressure P3 of the fluid in the supply line; and a differential pressure controller connected to the control valve, to the flexible tube pressure sensor, and to the fluid supply pressure sensor, and, when a ratio of the pressure P1 of the pressurized fluid in the flexible tube to the pressure P3 of the fluid in the fluid supply line is less than a predetermined ratio of at least 3 to 1, the differential pressure controller sends a signal to the control valve to open, in order to allow the pressurized fluid in the pressurized fluid source at the pressure of P2 to enter the flexible tube, and, when the ratio of the pressure P1 of the pressurized fluid in the flexible tube to the pressure P3 of the fluid in the fluid supply line equals the predetermined ratio, the differential pressure controller sends a signal to the control valve to close.

30. The dry fire protection sprinkler according to claim 29, wherein the sprinkler frame has frame arms that form a hub that is spaced from the outlet orifice.

31. The dry fire protection sprinkler according to claim 30, further comprising a deflector connected to the hub of the sprinkler frame.

32. The dry fire protection sprinkler according to claim 29, wherein the outlet end of the flexible tube is threadably connected to the sprinkler frame.

33. The dry fire protection sprinkler according to claim 29, further comprising a pressure indicator connected to the flexible tube, the pressure indicator being configured to indicate the pressure of the pressurized fluid in the flexible tube.

34. The dry fire protection sprinkler according to claim 33, wherein the pressure indicator is at least one of an analog pressure monitor and a digital pressure monitor.

35. The dry sprinkler according to claim 33, wherein the pressure indicator is constructed to communicate with an alarm system.

36. The dry fire protection sprinkler according to claim 35, wherein the alarm system notifies an operator if the pressure of the pressurized fluid in the flexible tube decreases to a certain pressure value.

37. The dry fire protection sprinkler according to claim 29, further comprising a flexible connector provided in the flexible tube and connected to the sealing cap of the outlet seal assembly.

38. The dry fire protection sprinkler according to claim 37, wherein the flexible connector is one of a chain and a cable.

39. The dry fire protection sprinkler according to claim 29, wherein the flexible tube is a corrugated metal hose.

40. The dry fire protection sprinkler according to claim 29, wherein the flexible tube is a corrugated plastic hose.

41. The dry fire protection sprinkler according to claim 29, wherein the spring washer of the outlet seal assembly is provided in the outlet orifice of the sprinkler frame, and the sealing cap of the outlet seal assembly is an annular disk that sits in the spring washer of the outlet seal assembly.

42. The dry fire protection sprinkler according to claim 41, wherein the annular disk of the outlet seal assembly has an annular groove, and the spring washer of the outlet seal assembly is positioned in the annular groove.

43. The dry fire protection sprinkler according to claim 1, wherein, when the thermally responsive element fails, the sealing cap of the outlet seal assembly is released, permitting the pressurized fluid in the flexible tube to flow through the outlet orifice.

44. The dry fire protection sprinkler according to claim 15, wherein, when the thermally responsive element fails, the sealing cap of the outlet seal assembly is released, releasing the inlet plug of the inlet seal assembly from the inlet orifice, and permitting the pressurized fluid in the flexible tube to flow through the outlet orifice.

45. The dry fire protection sprinkler according to claim 29, wherein, when the thermally responsive element fails, the sealing cap of the outlet seal assembly is released, permitting the pressurized fluid in the flexible tube to flow through the outlet orifice.

* * * * *